United States Patent
VanderVeer

(10) Patent No.: US 10,434,151 B1
(45) Date of Patent: *Oct. 8, 2019

(54) METHOD FOR TREATING AND MAINTAINING SKIN

(71) Applicant: Evance, LLC, Portland, OR (US)

(72) Inventor: Elizabeth VanderVeer, Lake Oswego, OR (US)

( * ) Notice: Subject to any disclaimer, the term of this patent is extended or adjusted under 35 U.S.C. 154(b) by 99 days.

This patent is subject to a terminal disclaimer.

(21) Appl. No.: 15/849,099

(22) Filed: Dec. 20, 2017

Related U.S. Application Data

(63) Continuation of application No. 15/186,288, filed on Jun. 17, 2016, now Pat. No. 9,867,874, which is a continuation of application No. 14/244,675, filed on Apr. 3, 2014, now Pat. No. 9,375,462.

(60) Provisional application No. 61/807,881, filed on Apr. 3, 2013.

(51) Int. Cl.
*A61K 36/28* (2006.01)
*A61K 38/48* (2006.01)
*A61K 36/87* (2006.01)
*A61K 9/00* (2006.01)
*A61K 36/287* (2006.01)
*A61K 33/30* (2006.01)
*A61K 33/34* (2006.01)

(52) U.S. Cl.
CPC ........ *A61K 38/4873* (2013.01); *A61K 9/0014* (2013.01); *A61K 33/30* (2013.01); *A61K 33/34* (2013.01); *A61K 36/28* (2013.01); *A61K 36/287* (2013.01); *A61K 36/87* (2013.01); *C12Y 304/22032* (2013.01); *C12Y 304/22033* (2013.01)

(58) Field of Classification Search
None
See application file for complete search history.

(56) References Cited

U.S. PATENT DOCUMENTS

| | | | |
|---|---|---|---|
| 6,579,543 B1 * | 6/2003 | McClung | A61K 8/345 424/401 |
| 7,217,417 B2 | 5/2007 | Knapp | |
| 9,375,462 B1 * | 6/2016 | VanderVeer | A61K 38/4873 |
| 9,867,874 B1 * | 1/2018 | VanderVeer | A61K 38/4873 |
| 2002/0127256 A1 | 9/2002 | Murad | |
| 2006/0003033 A1 | 1/2006 | McClellan | |
| 2006/0018867 A1 | 1/2006 | Kawasaki | |
| 2006/0165644 A1 | 7/2006 | Tanaka | |
| 2009/0162304 A1 | 6/2009 | DiLeva | |
| 2010/0150854 A1 | 6/2010 | Schmaus | |
| 2011/0020443 A1 | 1/2011 | Liu | |
| 2013/0064876 A1 | 3/2013 | Petit | |
| 2015/0064285 A1 * | 3/2015 | Liu | A61K 31/191 424/681 |

OTHER PUBLICATIONS

Khandpur S, Sharma VK & Sumanth K, Topical immunomodulators in dermatology, J Postgrad Med Jun. 2004, pp. 131-139, vol. 50 Issue 2, Medknow Publications, Mumbai, India.

* cited by examiner

*Primary Examiner* — Ralph J Gitomer
(74) *Attorney, Agent, or Firm* — Bert P. Krages

(57) ABSTRACT

A method of topically using a combination of *Arnica montana* extract, bromelain, *Calendula* extract, daisy flower extract, grape seed extract, copper, and zinc contained in a carrier to promote skin health and healing.

19 Claims, No Drawings

METHOD FOR TREATING AND MAINTAINING SKIN

CROSS-REFERENCED TO RELATED APPLICATIONS

This is a continuation application which claims the benefit of nonprovisional application Ser. No. 15/186,288, now U.S. Pat. No. 9,867,874, which was filed on Jun. 17, 2016, which in turn claims the benefit of nonprovisional application Ser. No. 14/244,675, now U.S. Pat. No. 9,375,462, which was filed on Apr. 3, 2014, which in turn claims the benefit of provisional application 61/807,881 which was filed on Apr. 3, 2013 and is incorporated by reference.

FIELD OF THE INVENTION

The invention relates generally to skin care products and methods of administration.

BACKGROUND OF THE INVENTION

The skin is a complex organ consisting of several layers which physiologically act together to either maintain itself in a healthy state or to respond to injuries in the form of trauma and skin disorders. The epidermis is composed of four or five sublayers, depending on which part of the body is being covered. The dermis is the layer beneath the epidermis and has two sublayers. The dermis also contains fibroblasts that produce collagen and elastin fibers. The hypodermis is the deepest layer of the skin and attaches to the dermis by collagen and elastin fibers.

Healthy skin is characterized by a process generally known as epidermal renewal in which the dead top cells flake off the stratum corneum over a period of weeks and are replaced by keratinocytes which are produced and pushed upwards by the other sublayers. The skin can be adversely affected by exposure to sunlight, overexposure to environmental pollutants, poor nutrition, and trauma in the form of cuts, burns, and bruises. In addition to trauma, skin conditions can be caused by disrupting the epidermal renewal process, altering the normal functioning of processes contained with the dermis, or changes to the blood vessels within the dermis.

The skin is capable of implementing healing processes depending on the type and degree of the skin condition affecting it. Wounds resulting in loss of integrity of the skin, such as cuts and abrasions, will generally undergo healing in sequential phases, i.e., hemostasis, inflammation, proliferation, and maturation. Such wounds are repaired in part by the migration of keratinocytes to close the wound. In addition, injured skin tissue is repaired by collagen deposition, collagen remodeling, and scar formation, The healing of other skin conditions proceeds in a similar manner, involving the processes of collagen production, fibroblast production, fibrocyte production, fibroplasia, and angiogenesis.

Commonly-recognized products for promoting healthy skin or treating skin conditions either exert an overall effect such as hydration or are primarily operative with respect to a single aspect of skin physiology. For example, moisturizers increase the hydration of skin by supplying an amount of water to the skin concurrent with an oil or grease to retard subsequent loss of the water. Products such as coal tar and salicylic acid help to normalize the manner and rate at which the cells are shed. However, they can cause adverse effects such as redness and dryness. Steroid creams, such as hydrocortisone cream, lessen inflammation and pruritus. Products such as benzoyl peroxide and alcohol have anti-bacterial effects but also tend to dry out the skin. Topical immunomodulators (TIMs) in the form of skin creams work by altering the immune system response. As such, the prior art teaches products that fail to enlist all the physiological pathways that are relevant to the healing of skin, and in some cases, can cause other skin problems. What is needed is a composition and method of treatment that accelerates the healing of skin conditions via concurrent physiological pathways.

SUMMARY OF THE INVENTION

The invention is a method that promotes the maintenance of healthy skin and expedites the healing of damaged skin by applying a combination of *Arnica montana* extract, bromelain, *Calendula* extract, daisy flower (*Bellis perennis*) extract, grapeseed extract, *Aloe vera*, copper, and zinc contained in a carrier. Topical application of the composition results in strengthening the epidermal barrier and accelerates the healing of the skin beyond the body's unaided healing processes or previously recognized conventional treatments.

The composition influences the various physiological mechanisms that modulate the control mechanisms that regulate the balance between cell growth and cell death, while concurrently mitigating the adverse effects of reactive oxygen species and fostering the removal of excess cellular debris from the skin. One of the features of the invention is that it uses a composition that comprises several constituents that have modulating properties with regard to apoptosis that ensure a multi-component base of compounds that contribute to its overall immunomodulating capabilities. The constituents that contribute immunomodulating properties to the invention that are believed to be the most dominant are grape seed extract, bromelain, and zinc. It is also believed that *Arnica Montana* extract, *Calendula* extract, *Aloe vera*, and copper components are contributors to apoptosis regulation. The combination of the constituents acts to balance the rates of cell growth and cell death and results in the orderly removal and renewal of keratinocytes. Of particular interest is trial work that shows that the composition induces the downregulation of hyperkeratotic cells.

The composition is formulated with extracts from several plant species, which bolsters the robustness of the immunomodulatory capability. Because the constituents have different bioavailabilities, dermal absorption rates, and dermal penetration depths, the combination of the immunomodulatory agents comprising the composition ensures a base that is more biochemically complex than would be the case with a base that contains a single constituent having such effect. As a result, the composition has a greater effectiveness than would be expected by aggregating the individual constituents.

The method is effective for use on a broad population. The skins of individuals vary significantly in their ability to absorb and process specific constituents. A significant factor is the normal individual genetic variability among populations with regard to the enzymes and transporters that carry out the physiologic functions of the skin. Likewise, the bioavailability of a substance can vary depending on the specific nature of an individual's skin condition or status. For example, some constituents tend to be absorbed more or less efficiently depending on whether the skin contains certain levels of fat or collagen, which can vary over time. Similarly, skin is subject to levels of stress which vary over time. For example, a skin that has recently been exposed to high levels of ultraviolet-B radiation will be in a different immunomodulatory state than skin which has not been so exposed. A skin care composition that is based on the constituents described in this specification is able to ensure a level of uptake that is capable of producing the desired physiologic effect throughout a diverse population.

By incorporating a broad base of immunomodulatory agents, the composition has a sustained effectiveness lasting at least several hours because the kinetic characteristics of the constituents cover a significant range of biochemical uptake, activity, and elimination. This overcomes a shortcoming of prior art immunomodulators because the absorption and effective period of such immunomodulators are not always sufficient to sustain the desired action throughout the course of the relevant period. Combining immunomodulatory agents that have different rates of metabolic processing thus enables the composition to work effectively over a more extended period of time.

The method of using the composition has been found to improve cell respiration and blood circulation, as well as having a marked effect in reducing inflammation and enhancing the production of collagen and elastin in the skin layers. It also promotes the regeneration of skin cells and the removal of damaged proteins. These effects are caused in part by regulating the production of transforming growth factor and vascular endothelial growth factor, and in regulating angiogenesis, which can be critical to healthy skin formation.

Another aspect of the method is the reduction of reactive oxygen species (ROS) such as those generated during exposure of the skin to ultraviolet-B and other forms of radiation. These species have the capacity to induce oxidative decomposition in the skin which in turn leads to the formation of toxic species as well as lipid peroxidation, both of which damage the skin and adversely affect its appearance. Another source of ROS are medical lasers that, while capable of being used beneficially to treat various skin conditions, can produce ROS and cause detrimental effects such as erythema and pigmentation changes. The topical administration of antioxidants, in combination with the other ingredients of the composition, can significantly reduce erythema-associated redness and other expressions of oxidative skin damage. In particular, the grapeseed extract and daisy flower extract provide substantial antioxidant content to the composition. The daisy flower extract can exert an additional effect by lightening the skin.

Bromelain promotes cellular debris removal. The extent to which the stratum corneum is composed of dead cells has a substantial effect on the texture and appearance of the skin and the timely removal of excess cellular debris is beneficial in this regard. Bromelain also de-ages the skin by taking away the dull dead skin and reducing the appearance of fine lines, enlarged pores, dullness, and wrinkles. Furthermore, the removal of cellular debris has a positive effect on suppressing recurrent outbreaks of acne by removing acne-producing bacteria from skin pores. This function, albeit physiologically distinct from immunoregulatory mechanism, has an unexpectedly positive effect on reducing skin inflamation.

Other constituents may be added to the composition to augment effectiveness. For example, hyaluronic acid improves skin pliability, retards transepidermal water loss, and increases the skin's water-retaining properties by acting as a humectant. Willow bark extract from Salix species encompasses salicylic acid, quercetin, and rutin which exert exfoliant and anti-inflammatory effects on the skin. In addition, willow bark extract has antimicrobial, antifungal, and antiviral properties that can promote protection of the skin from infectious agents. Marsh mallow extract, derived from *Althea officinalis*, contains mucilagenous polysaccharides and antioxidants which are useful for reducing the irritation of skin tissue and for enhancing the barrier function of the skin. Date fruit extract, derived from *Phoenix* species such as *P. dactylifera*, acts as an emollient and promotes the delivery of the constituents of the composition into the deeper epidermal layers.

DESCRIPTION OF THE PREFERRED EMBODIMENT

The present invention is a method of using a composition, described in Table 1, that comprises constituents that simultaneously affect several physiological pathways with synergistic effect. The percentages listed adjacent to each constituent are the ranges of the constituents in terms of weight and the specific concentrations by weight in the formulation for a skin care serum. Note that the expressed ranges should be viewed as relative proportions with respect to each constituent and do not necessarily reflect the actual percentages contained in the formulated product. It should also be recognized that the ranges are useful starting points for preparing a formulation and should not be viewed as restrictions on the scope of ranges in which a formulation may be prepared. The composition may contain other constituents that, while providing a benefit to skin health, are optional. Examples of such compounds are magnesium, hyaluronic acid, and marsh mallow extract. A preferred embodiment of the composition used in the invention is set forth in the column labeled "serum formulation" in Table 1.

TABLE 1

Formulations

| Constituent | Range of concentrations | Serum Formulation |
|---|---|---|
| *Arnica montana* extract: | 0.50%-5% | 1.0% |
| Bromelain: | 0.05%-5% | 0.25% |
| *Calendula* extract: | 0.50%-5% | 1.0% |
| Daisy Flower extract: | 0.50%-5% | 1.0% |
| Grape seed extract: | 0.50%-5% | 1.0% |
| *Aloe vera*: | 5%-95% | 20% |
| Willow Bark: | 0.50%-5% | 1.0% |
| Marsh Mallow extract: | 0.50%-5% | 0.0% |
| Date Fruit extract: | 0.50%-5% | 1.0% |
| Zinc: | up to 25% as zinc | 1.0% |
| Copper: | up to 0.5% as copper | 0.5% |
| Magnesium: | up to 5% as Mg | 0.1% |
| Hyaluronic Acid: | 0.10%-1% | 1.0% |

The composition encompasses several types of extracts. As a general rule, it is desirable to use extracts in which the extracted material is at or near the point of maximum concentration. This is generally done by placing the maximum amount of plant material that can reasonably be accommodated by the extracting fluid, consistent with efficacious extraction practices. The extracts can be made using any of the extraction methods that are known within the art and with extractants such as water, alcohol, or oils.

For the purposes the composition described above, the *Arnica montana* extract can be made by extracting 250 ml of powdered dried *Arnica* flowers with 1 liter of water, the *Calendula* extract can be made by extracting 400 grams of dried flowers with 1 liter of water, daisy flower extract can be made by extracting 100 grams of dried powdered flowers and pedicels with 1 liter at about 80° C., and date (*Phoenix dactylifera*) fruit extract can be prepared by extracting about 275 grams of fruit in 1 liter of heated water. Grape seed extract is incorporated into the composition as a powder containing not less than 95% oligomeric proanthocyanidin complexes (OPCs).

Bromelain, may be added to the composition as a powder that contains 2000 gelatin-dissolving units per gram of powder. Willow bark can be added in the form of powdered bark and marsh mallow can be added in the form of powdered leaves and roots. Hyaluronic acid can be added in powder form as sodium hyaluronate. *Aloe vera* is an extract from the *Aloe vera* plant may provided in the form of *Aloe* gel, which is produced by physically separating the gel from the leaves of the plant. It may also be provided in the form of a powder. Zinc made added in the form an organic or inorganic salt such as zinc picolinate, zinc acetate, zinc gluconate, zinc monomethionine, zinc pyrithione, and zinc oxide. Similarly, copper can be incorporated into the composition in various salt forms including copper citrate, copper gluconate, and copper tripeptide. Magnesium may be incorporated in organic and inorganic salt forms such as magnesium aspertate.

Combinations of the ingredients described above can be incorporated into various forms of carriers such as tinctures, gels, powders, lotions, oils, serums, and creams. Such carriers are well known in the fields of pharmacology, skin care products, and cosmetics. Examples of specific carrier constituents include jojoba oil, olive oil, grapeseed oil, aloe vera, and avocado oil.

Optionally, the ingredients can be incorporated into a concealer or camouflage type of makeup. This embodiment of the composition is prepared by making a concealer base that contains pigments with sufficient opacity to hide skin conditions when the composition is applied to the skin. Such pigments may include substances such as titanium dioxide, iron oxides, mica, magnesium stearate, talc, magnesium carbonate, zinc stearate, bismuth oxychloride, and boron nitride. The pigments are held in a binder that can be prepared from one or more ingredients suitable for containing the active ingredients described above. Such ingredients may include water, petroleum distillates, beeswax, cyclomethicone, isostearyl neopentanoate, ozokerite, sorbitan sesquioleate, sodium borate, tetrasodium EDTA, methylparaben, propylparabe, mineral oil, isopropyl palmitate, carnauba (copernicia cerifera) wax, allantoin, octyl palmitate, dimethicone, isopropyl lanolate, polysorbate 80, imidazolidinyl urea, quaternium 15, caprylic/capric triglyceride, propylene glycol, dimethicone, cetyl alcohol, cyclomethicone, glyceryl stearate, sorbitan stearate, peg-40 stearate, PEG-100 stearate, methylchloroisothiazolinone, methylisothiazolinone, *Helianthus annuus* (sunflower) seed oil, cyclopentasiloxane, cyclotetrasiloxane, and triethanolamine. The concealer embodiment can be prepared in a variety of shades and colors to look like a natural skin tone or to contrast with a particular type of skin condition. For example, white can be used to offset the appearance of bruising and green and blue can counteract red patches on the skin, such as those caused by rosacea.

The preferred regimen for the method is that the composition should be applied topically to the skin at least once daily, although more frequent application may be indicated depending on the nature and extent of the skin condition. The exact time of day for the application of the composition for promotion of general skin health is not critical but it is recommended that the composition should be applied at least five days per week to ensure a sustained effect. The application interval can be increased with beneficial effects on certain skin conditions and preferably should be applied shortly after an event that may cause a skin condition, or in any case, shortly after the appearance of symptoms.

As described previously, the composition acts to down regulate or modulate the hyperproliferation of keratocytes and is useful in controlling skin conditions in which hyperproliferation is manifested. Trial work has shown that the composition has a beneficial effect on skin comprising preneoplastic and neoplastic cells by reducing the presence of such cells subsequent to topical application.

The method of using composition has general applicability for the treatment of erythematous skin and atopic dermatitis, particularly skin that is irritated or inflamed due to bacteria, viruses, fungi, allergens, insect bites, and sunburn. Notably, the method is useful against bacterial infections of the type associated with acne or caused by *Staphylococcus aureus* or *Streptococcus* species. It is also useful against fungal infections caused by *Tinea corporas, Tenea pedis*, and *Candida* species as well as viral infections such as those caused by herpes simplex viruses, human herpes virus-3, and molluscum contagiosum viruses.

The method of using the composition can prevent or reduce erythema of the skin if topically applied to the skin within 30 minutes of laser irradiation or a hypodermic injection. It is likewise effective when applied to skin irritated by urushiol which is an oil produced by members of the *Toxicodendron* genus of plants (e.g, poison ivy, poison oak). In addition, the composition promotes healing of open skin wounds such as abrasions, lacerations, and punctures; as well as closed skin hematomas.

As would be apparent to a person skilled in the art, a number of variations and modifications can be made to the method described above without departing from the spirit and scope of the present invention.

The invention claimed is:

1. A method of treating skin comprising the topical application of a composition to skin having a condition selected from the group consisting of:
   skin in which enhanced collagen production is desired,
   skin that has been exposed to laser irradiation within the previous 30 minutes,
   hyperkeratotic lesions,
   open wounds,
   hematomas,
   skin containing preneoplastic or neoplastic cells,
   urushiol-induced contact dermatitis,
   skin infected by viruses,
   skin infected by bacteria, and
   skin infected by fungi;
wherein said composition is comprised of effective amounts of *Arnica montana* extract, bromelain, *Calendula* extract, daisy flower extract, grape seed extract, zinc, and copper.

2. The method of claim 1 in which the following constituents that are formulated by weight according to the following ranges of parts: *Arnica montana* extract, 0.5-5%; bromelain, 0.05%-5%; *Calendula* extract, 0.5-5%; daisy flower extract, 0.5-5%; grape seed extract, 0.5-5%; zinc (as zinc), 0.5-25%; and copper (as copper), 0.05% to 0.5%.

3. The method of claim 1 in which the following constituents are formulated by weight such that the composition contains the following minimum percentages by parts: *Arnica montana* extract, 0.5%; bromelain, 0.05%; *Calendula* extract, 0.5%; daisy flower extract, 0.5%; grape seed extract, 0.5%; zinc (as zinc), 0.5%; and copper (as copper), 0.05%.

4. The method of claim 1, wherein the skin in need comprises skin in which enhanced collagen production is desired.

5. The method of claim 1 wherein the skin in need comprises areas of skin that have been exposed to laser irradiation and said composition is topically applied within 30 minutes of the termination of said laser irradiation.

6. The method of claim 1 wherein the skin in need comprises erythematous skin.

7. The method of claim 1 wherein the composition is topically applied to skin having hyperkeratotic lesions.

8. The method of claim 1 wherein the skin in need is skin having an open wound.

9. The method of claim 1 wherein the skin in need is skin affected by a hematoma.

10. The method of claim 1 wherein the skin in need contains preneoplastic or neoplastic cells.

11. The method of claim 1 wherein the skin in need is skin infected by a virus, bacteria, or fungi.

12. The method of claim 1 wherein the skin in need is skin infected by viruses.

13. The method of claim 1 wherein the skin in need is skin infected by bacteria.

14. The method of claim 1 wherein the skin in need is skin infected by fungi.

15. The method of claim 1 in which the composition further comprises pigments with sufficient opacity to hide skin conditions when the composition is applied to the skin.

16. A method of enhancing collagen production in skin comprising the topical application of a composition which is comprised of effective amounts of *Arnica montana* extract, bromelain, *Calendula* extract, daisy flower extract, grape seed extract, zinc, and copper.

17. The method of claim 16 in which the following constituents are formulated by weight such that the composition contains the following minimum percentages by parts: *Arnica montana* extract, 0.5%; bromelain, 0.05%; *Calendula* extract, 0.5%; daisy flower extract, 0.5%; grape seed extract, 0.5%; zinc (as zinc), 0.5%; and copper (as copper), 0.05%.

18. A method of promoting the maintenance of healthy skin comprising the topical application of a composition to skin wherein said composition is comprised of effective amounts of *Arnica montana* extract, bromelain, *Calendula* extract, daisy flower extract, grape seed extract, zinc, and copper.

19. The method of claim 18 in which the following constituents are formulated by weight such that the composition contains the following minimum percentages by parts: *Arnica montana* extract, 0.5%; bromelain, 0.05%; *Calendula* extract, 0.5%; daisy flower extract, 0.5%; grape seed extract, 0.5%; zinc (as zinc), 0.5%; and copper (as copper), 0.05%.

* * * * *